(12) United States Patent
Sheehan et al.

(10) Patent No.: US 8,163,464 B2
(45) Date of Patent: Apr. 24, 2012

(54) PROPANOATES AND PROCESSES FOR PREPARING THE SAME

(75) Inventors: Michael T. Sheehan, Corpus Christi, TX (US); James R. Sounik, Waynesville, OH (US); George W. Clark, III, Dublin, OH (US)

(73) Assignee: Du Pont Electronic Polymers L.P., Research Triangle Park, NC (US)

( * ) Notice: Subject to any disclaimer, the term of this patent is extended or adjusted under 35 U.S.C. 154(b) by 442 days.

(21) Appl. No.: 12/462,447

(22) Filed: Aug. 4, 2009

(65) Prior Publication Data

US 2010/0047714 A1 Feb. 25, 2010

Related U.S. Application Data

(60) Provisional application No. 61/189,963, filed on Aug. 25, 2008.

(51) Int. Cl.
| | |
|---|---|
| C07C 67/31 | (2006.01) |
| C07C 67/327 | (2006.01) |
| C07C 69/734 | (2006.01) |
| G03F 7/004 | (2006.01) |

(52) U.S. Cl. .................. 430/286.1; 560/103; 430/270.1
(58) Field of Classification Search .................. None
See application file for complete search history.

(56) References Cited

U.S. PATENT DOCUMENTS

| | | | | |
|---|---|---|---|---|
| 3,585,216 | A | * | 6/1971 | Cross .............................. 549/415 |
| 5,151,443 | A | | 9/1992 | Henrick |
| 5,278,210 | A | | 1/1994 | Morini et al. |
| 6,495,719 | B2 | | 12/2002 | Lan-Hargest et al. |
| 7,002,037 | B2 | * | 2/2006 | Andersson et al. .............. 560/27 |
| 2002/0143052 | A1 | | 10/2002 | Lan-Hargest et al. |
| 2002/0177726 | A1 | * | 11/2002 | Kumar et al. ................... 560/60 |
| 2009/0124656 | A1 | | 5/2009 | Parmenon et al. |

FOREIGN PATENT DOCUMENTS

| | | |
|---|---|---|
| WO | WO 88/03805 | 6/1988 |
| WO | WO 2006/079719 | 3/2006 |
| WO | WO 2007/079861 | 7/2007 |

* cited by examiner

*Primary Examiner* — Cynthia Hamilton
(74) *Attorney, Agent, or Firm* — James J. Mullen

(57) ABSTRACT

A process for preparing proponates which comprises the steps of (i) supplying a solution of methanol containing 4-hydroxyphenylmethylcarbinol, (ii) subjecting said solution to an acid catalyzed displacement reaction for a sufficient period of time and under suitable conditions of temperature and pressure to convert substantially all of said carbinol to 4-hydroxyphenylmethylcarbinol methyl ether in solution, (iii) replacing the methanol in said ether containing solution with a second solvent and (iv) reacting the ether containing ethyl lactate solution with a suitable acid catalyst for a sufficient period of time and under suitable conditions of temperature and pressure to form said propanoates. New compositions of matter which comprise the propanoates, prepared in the above manner, have application in the electronic chemicals market such as in a photoresist composition.

14 Claims, No Drawings

PROPANOATES AND PROCESSES FOR PREPARING THE SAME

RELATED PATENT APPLICATIONS

This new utility patent application is based upon U.S. provisional patent application Ser. No. 61/189,963 filed on Aug. 25, 2008 and is entitled to the priority date thereof.

BACKGROUND OF THE INVENTION

1. Field of the Invention

The present invention relates to a new class of propanoates (generally referred to herein as EHPEP) and processes for their production directly from 4-hydroxymethyl-carbinol (HPMC) and/or from 4-hydroxyphenylmethylcarbinol methyl ether (HPME) and which have utility in the electronic chemicals market such as photoresist compositions.

2. Description of the Prior Art

The following prior art references are disclosed for informational purposes. While propanoic acid is generally disclosed in WO 2007079861; WO 2006079719; US 2002143052; U.S. Pat. No. 6,495,719; U.S. Pat. No. 5,278,210; U.S. Pat. No. 5,151,443; and WO 8803805, none of these references disclose the new class of propanoates described and claimed in the present patent application, much less a process for preparing the same and their utility as such in photoresists.

All of the above-cited prior art and any other references mentioned herein are incorporated herein by reference in their entirety.

SUMMARY OF THE INVENTION

The present invention, in part, discloses a new class of propanoates (EHPEP) of the structural formula set forth herein and which EHPEP has unique characteristics, particularly in the photoresist art. Another aspect of the present invention is a process for preparing the propanoates which comprises the steps of (i) supplying a solution of methanol containing 4-hydroxymethyl-carbinol (HPMC), (ii) subjecting said solution to an acid catalyzed displacement reaction for a sufficient period of time and under suitable conditions of temperature and pressure to convert substantially all of said HPMC to 4-hydroxyphenylmethylcarbinol methyl ether (HPME) in said solution, and (iii) replacing the methanol from said ether containing solution with a second solvent such as ethyl lactate, (iv) reacting the HPME in said second solvent with a suitable acid catalyst in solution with second solvent for a sufficient period of time and under suitable conditions of temperature and pressure to form the propanoates. One of the most important characteristics of the new propanoates is the fact that when used in a photoresist composition it acts as an absorbance modifier and thus provides a substantially improved photoresist.

DETAILED DESCRIPTION OF THE INVENTION

The present invention provides, in part, new propanoates (EHPEP) having the following structure:

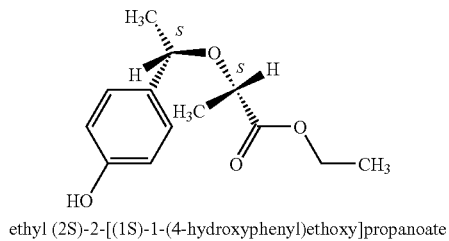

ethyl (2S)-2-[(1S)-1-(4-hydroxyphenyl)ethoxy]propanoate

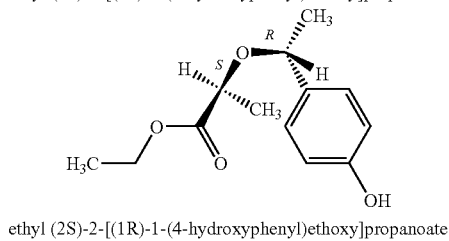

ethyl (2S)-2-[(1R)-1-(4-hydroxyphenyl)ethoxy]propanoate and mixtures thereof.

The above compounds can also be named (a) propanoic acid, 2-[(1S)-1-(4-hydroxyphenyl)ethoxy]-, ethyl ester, (2S) and (b) propanoic acid, 2-[(1R)-1-(4-hydroxyphenyl) ethoxy]-, ethyl ester, (2S). These are collectively (such as mixtures) and individually called EHPEP herein The present invention provides a novel EHPEP and a novel process for preparing EHPEP which comprises the steps of (i) supplying a solution of methanol containing 4-hydroxyphenylmethylcarbinol (HPMC), (ii) subjecting said solution to an acid catalyzed displacement reaction for a sufficient period of time and under suitable conditions of temperature and pressure to convert substantially all of said carbinol to 4-hydroxyphenylmethylcarbinol methyl ether in solution, (iii) replacing the methanol in said ether containing solution with a second solvent such as ethyl lactate, and (iv) reacting the ether containing ethyl lactate solution with a suitable acid catalyst contained in a second solvent solution for a sufficient period of time and under suitable conditions of temperature and pressure to form the EHPEP/propanoates.

More specifically, the present invention is directed, in part, to a unique, cost-efficient process for preparing the new class of propanoates.

In the first step of providing a solution of methanol containing HPMC, this compound is known in the art as exemplified by US 2005-0250042 A1, published on Nov. 10, 2005; this publication discloses processes for preparing HPMC. HPMC can also be prepared from 4-hydroxyacetophenone (4HAP).

In the second step, HPMC is subject to an acid catalyzed displacement reaction in order to convert it to its methyl ether form, i.e. HPME. This step can be carried out by use of an acid ion exchange resin such as Amberlyst-15 (Rohm and Haas product), Rohm and Haas CT-200, or M31 (Dow Product). The HPMC material is supplied in a methanol solvent wherein the HPMC is dissolved therein. The concentration of HPMC in solution is from about 1% to about 50% by weight, preferably from about 15% to about 30% by weight. This conversion takes place by merely contacting said HPMC containing methanol solution with, e.g. the A-15 material either by running the solution through a fixed bed of A-15 or merely mixing the two materials together for a sufficient period of time and under suitable conditions of temperature and pressure. The temperature of the conversion step is not critical and can be from about 0 C to about 100 C and the pressure is also not critical, but can be from about 0 psig to about 10 psig, or even conducted under vacuum. The conversion time is also not critical and is long as necessary to convert the HPMC to the methyl ether form, HPME. This time can be as long as several days at room temperature to as short as 3-4 minutes at 45 C. The critical factor in this conversion step is the conversion must convert substantially all of the HPMC to the methyl ether form before the solvent swap/replacement step takes place. It is desirable that the conversion be at least 90% complete, preferably at least 95% complete. It is another object in this step to reduce the ionic metals content to low parts per billion (ppb) levels, preferably less than about 25 ppb for each of the metal ions present.

The third step is a solvent swap/replacement procedure which is carried out with the use of ethyl lactate which removes the methanol solvent and results in the HPME being totally dissolved in the ethyl lactate solution.

The fourth step is the interaction of the HPME/ethyl lactate solution by the use of a suitable acid catalyst in ethyl lactate under suitable conditions of temperature and pressure to form the desired end EHPEP/propanoate. Thus, the ethyl lactate acts as a solvent and a reactant.

The catalyst employed in this fourth step present invention process is selected from the group $H_2SO_4$, HCl, $H_3PO_4$, para-toluene sulfonic acid, methane sulfonic acid, trifluoroacetic acid, and trichloroacetic acid, and mixtures thereof. Generally, Lewis acids and protic acids having a pKa of less than about 4.75 are suitable.

The catalyst is used in any amount in order to facilitate the reaction to yield the EHPEP/propanoates which have the structures set forth herein. Such amounts generally are from about one part per million (ppm) to about 5 ppm, preferably from about 1 to about 3 ppm.

The temperature employed in this fourth step is generally less than about 120° C., more specifically from about 0° C. to about 120° C., preferably from about 40° C. to about 60° C. The reaction pressure may be subatmospheric, atmospheric, or superatmospheric, preferably from about 10 to about 200 mm Hg (millimeters of mercury).

The length of time which this reaction step is conducted is not critical and the only requirement is that the reaction be conducted for a period of time sufficient to form EHPEP. Generally, this period is at least five minutes and may be as long as 25 hours.

After this fourth step, there remains the reaction mixture (i.e. acid catalyst+EHPEP). The desired end product (EHPEP) is recovered from the reaction mixture by crystallization.

The following is a more detailed and specific summary of the unique processes of the present invention EHPEP Synthesis Formation of 4HPME from 4HPMC 4-hydroxyphenylmethylcarbinol (4-HPMC) dissolved in methanol at 10-30 wt. % is passed across strong sulfonic acid ion exchange resin such as Rohm and Haas CT-200 or Amberlyst 15 in order to react the 4-HPMC with methanol and form 4-hydroxyphenylmethyl ether in methanol and to reduce the ionic metals content to low ppb levels (preferably <5 ppb each of Na, K, Ca, Fe, Ni, Cr, Mg, Mn, Pb, Zn, Al and Cu).

Removal of the ionic impurities at this step is important to be able to achieve a final product with low metals.

Solvent Swap of 4HPME in Methanol to 4HPME in Ethyl Lactate

4HPMC dissolved in methanol is placed in a heated and stirred round bottom glass flask fitted with vacuum and side arm condenser and cold trap. Ethyl lactate is added as methanol is removed at approximately 50 deg. C. and 50 mm Torr. Generally, the resulting analytical data indicates less than 0.1 wt. % methanol in the HPME/ethyl lactate solution. HPME is approximately 15 wt. % soluble in ethyl lactate at room temperature.

Addition of Acid Catalyst and Reaction to EHPEP

Fifteen wt. % 4HPME in ethyl lactate is placed in a heated and stirred round bottom glass flask fitted with vacuum and side arm condenser and cold trap. P-toluenesulfonic acid monohydrate (p-TSA) dissolved in ethyl lactate is added to the reactor with mixing to achieve a concentration of about 2 ppm p-TSA. The contents are heated to about 50 deg. C. Pressure is regulated with N2 purge to maintain 50-100 Torr and by-product methanol along with some ethyl lactate are distilled and collected in the cold trap. Ethyl lactate is added to keep the concentration approximately at the same total volume to account for distilled methanol and ethyl lactate removal. After approximately 12-14 hours, >95% of the 4HPME is converted to a mixture of Propanoic acid, 2-[(1S)-1-(4-hydroxyphenyl)ethoxy]-, ethyl ester, (2S)- and Propanoic acid, 2-[(1R)-1-(4-hydroxyphenyl)ethoxy]-, ethyl ester, (2S)-(collectively and individually known as EHPEP).

Isolation

The reaction mixture is slowly cooled to below 5 deg. C with mixing to allow for the crystallization of the EHPEP. After holding at the target temperature for approximately 2 hours, the crystals are separated by filtration or other normal means and the wet cake is washed with a solvent which effectively removes the residual p-TSA and ethyl lactate but does not dissolve the EHPEP. Examples of such a solvent are deionized water (to maintain low metals), n-hexane or mixed hexanes, n-heptane or mixed heptanes and similar solvents. Cold ethyl lactate can also be used to remove the pTSA but some dissolution of the EHPEP will result in yield loss. The washed crystals are them placed in a vacuum drying oven to remove the residual solvents. Alternately, the wet crystals can be dissolved in ethyl lactate in a reactor and heated under vacuum to distill off the washing solvent resulting in approximately 6-15 wt. % solution of EHPEP in ethyl lactate.

The above procedure is more vividly illustrated by the schematic set forth below. In this case, 4HAP is used as the starting material to prepare HPMC.

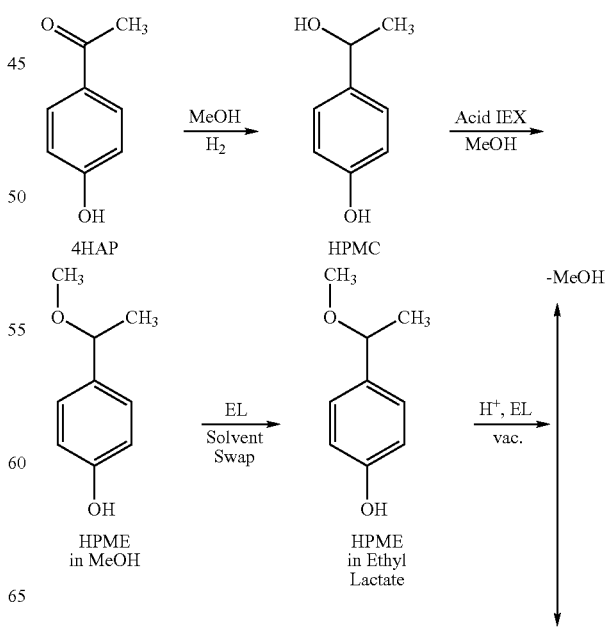

-continued

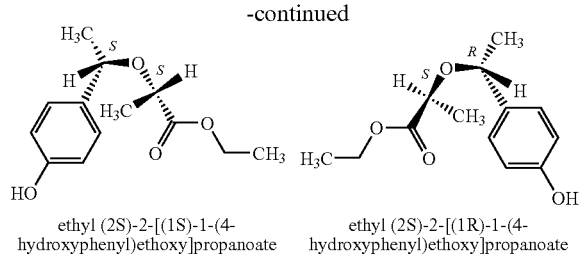

ethyl (2S)-2-[(1S)-1-(4-hydroxyphenyl)ethoxy]propanoate    ethyl (2S)-2-[(1R)-1-(4-hydroxyphenyl)ethoxy]propanoate In conjunction with the utility of the new class of propanoates, it has been found that the incorporation of these propanoates into polymer compositions which are being used in photoresist compositions results in an unexpected enhancement of the absorbancy of the overall photoresist.

Another inventive feature of the present invention is the use of the propanoates with homopolymers, copolymers, terpolymers, and the like to form photoresist compositions. The polymers used herein can be from various monomers used in the art the make photoresists.

Thus one embodiment of this invention involves the combination of the propanoates with the polymers formed from the polymerization of various monomers such as styrenics, olefinics, acrylate-type monomers, and the like known in the photoresist art. Various type monomers can be used in the inventive step of the present invention, and are exemplified, without limitation, below.

Styrenics include, without limitation, a substituted styrene monomer of formula I,

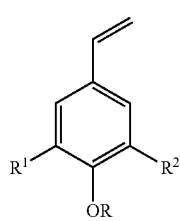

I wherein R is either —C(O)R$^5$ or —R$^5$; in this formula I, the following are the definitions:
i) R$^1$ and R$^2$ are the same or different and independently selected from the group consisting of:
hydrogen;
fluorine, chlorine or bromine;
alkyl or fluoroalkyl group having the formula $C_nH_xF_y$ where n is an integer from 1 to 4, x and y are integers from 0 to 2n+1, and the sum of x and y is 2n+1; and
phenyl or tolyl;
ii) R$^3$ is selected from the group consisting of:
hydrogen; and
methyl, ethyl, n-propyl, iso-propyl, n-butyl, i-butyl or t-butyl;
iii) R$^4$ is selected from the group consisting of methyl, ethyl, n-propyl, i-propyl, n-butyl, i-butyl, t-butyl, t-amyl, benzyl, cyclohexyl, 9-anthracenyl, 2-hydroxyethyl, cinnamyl, adamantly, methyl or ethyl adamantly, isobornyl, 2-ethoxyethyl, n-heptyl, n-hexyl, 2-hydroxypropyl, 2-ethylbutyl, 2-methoxypropyl, 2-(2-methoxyethoxyl), 2-naphthyl, 2-phenylethyl, phenyl, and the like.
iv) R$^5$ is $C_1$-$C_5$ alkyl, either straight or branch chain.

Other monomers include, without limitation, an acrylate monomer having the formula II,

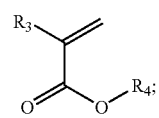

II wherein the definition of R3 and R4 are the same as set forth above.

In conjunction with Formula II (an acrylate monomer) set forth herein, some preferred acrylate monomers are (1) MAA—methyl adamantyl acrylate, (2) MAMA—methyl adamantyl methacrylate, (3) EAA—ethyl adamantyl acrylate, (4) EAMA—ethyl adamantyl methacrylate, (5) ETCDA—ethyl tricyclodecanyl acrylate, (6) ETCDMA—ethyl tricyclodecanyl methacrylate, (7) PAMA—propyl adamantyl methacrylate, (8) MBAMA—methoxybutyl adamantyl methacrylate, (9) MBAA—methoxybutyl adamantyl acrylate, (10) isobornylacrylate, (11) isobornylmethacrylate, (12). cyclohexylacrylate, and (13) cyclohexylmethacrylate. Other preferred acrylate monomers which can be used are (14) 2-methyl-2-adamantyl methacrylate; (15) 2-ethyl-2-adamantyl methacrylate; (16) 3-hydroxy-1-adamantyl methacrylate; (17) 3-hydroxy-1-adamantyl acrylate; (18) 2-methyl-2-adamantyl acrylate; (19) 2-ethyl-2-adamantyl acrylate; (20) 2-hydroxy-1,1,2-trimethylpropyl acrylate; (21) 5-oxo-4-oxatricyclo-non-2-yl acrylate; (22) 2-hydroxy-1,1,2-trimethylpropyl 2-methacrylate; (23) 2-methyl-1-adamantyl methacrylate; (24) 2-ethyl-1-adamantyl methacrylate; (25) 5-oxotetrahydrofuran-3-yl acrylate; (26) 3-hydroxy-1-adamantyl methylacrylate; (27) 5-oxotetrahydrofuran-3-yl 2-methylacrylate; (28) 5-oxo-4-oxatricyclo-non-2-yl 2 methylacrylate.

Additional acrylates and other monomers that may be used in the present invention with the substituted styrene to form various copolymers include the following materials: Monodecyl maleate; 2-hydroxy ethyl methacrylate; isodecyl methacrylate; hydroxy propyl methacrylate; isobutyl methacrylate; lauryl methacrylate; hydroxy propyl acrylate; methyl acrylate; t-butylaminoethyl methacrylate; isocyanatoethyl methacrylate; tributyltin methacrylate; sulfoethyl methacrylate; butyl vinyl ether blocked methacrylic acid; t-butyl methacrylate; 2-phenoxy ethyl methacrylate; acetoacetoxyethyl methacrylate; 2-phenoxy ethyl acrylate; 2-ethoxy ethoxy ethyl acrylate; beta-carboxyethyl acrylate; maleic anhydride; isobornyl methacrylate; isobornyl acrylate; methyl methacrylate; ethyl acrylate; 2-ethyl hexyl methacrylate; 2-ethyl hexyl acrylate; glycidyl methacrylate; N-butyl acrylate; acrolein; 2-diethylaminoethyl methacrylate; allyl methacrylate; vinyl oxazoline ester of meso methacrylate; itaconic acid; acrylic acid; N-butyl methacrylate; ethyl methacrylate; hydroxy ethyl acrylate; acrylamide oil; acrylonitrile; methacrylic acid; and stearyl methacrylate.

Other monomers include one or more ethylenically unsaturated copolymerizable monomers (EUCM) selected from the group consisting of styrene, 4-methylstyrene, styrene alkoxide wherein the alkyl portion is $C_1$-$C_5$ straight or branch chain, maleic anhydride, dialkyl maleate, dialkyl fumarate and vinyl chloride, wherein alkyl is having 1 to 4 carbon atoms, comprising the following steps.

Co-polymers having polyhydroxystyrene (PHS) and one or more of the above acrylate monomers are some of the materials that are used in the novel processes of the present invention.

The propanoates are added after the polymerization/purification steps have been formed and the polymer is generally in a solvent which is suitable for use in the photoresist composition. The polymerization and purification procedures used herein are those which are disclosed in U.S. Pat. No. 6,864,324; U.S. Pat. No. 6,787,611; U.S. Pat. No. 7,148,320; and U.S. Pat. No. 7,312,281. All of these patents are incorporate herein by reference in toto. The propanoates also are basically in the same solvent system and can be added to the polymers at this point. The amount of propanoates used with the polymers is less than about 5.0 weight percent of the polymer weight percent, and preferably from about 0.01 to about 3.5 wt. percent, and more preferably from about 0.05 to about 2.0 wt. percent. A preferred photoresist composition would contain polyhydrostyrene, t-butyl acrylate and EHPEP.

In addition to the use of EHPEP/propanoates in the microelectronic chemicals market, such EHPEP can be employed in standard applications such as varnishes, aniline printing inks, raw materials for epoxy resins, copying paper, tackifiers for rubber, and crude oil separators and other applications as stated herein.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLES

Example 1

To a 5-L round bottom glass reactor fitted with a heating mantle, thermocouple temperature indicator, overhead stirrer, vacuum, $N_2$ purge and sidearm condenser with a dry ice and isopropanol cooled glass distillate trap, 1103.6 g of 28 wt. % 4-hydroxyphenylmethylcarbinol (HPME) in methanol and 956.4 g. of (−)-ethyl L-lactate was added to achieve approximately a 15 wt. % mixture of 4HPME. The reaction contents were heated to 50 deg. C. at ~200 Torr and the methanol was removed by vacuum distillation to less than 0.1 wt. %.

To the reaction contents of 4HPME in (−)-ethyl L-lactate was added 1.31 g of a 0.402 wt. % p-toluenesulfonic acid monohydrate solution in (−)-ethyl L-lactate to achieve a pTSA concentration of 17 ppm vs. 4HPME or 2.6 ppm vs. the total contents. The pressure was held at 200 Torr and the temperature was held at 50 deg. C. The methanol byproduct was distilled from the reaction along with some (−)-ethyl L-lactate which was replaced during the reaction to maintain ~15 wt. % solids. The reaction was run for 12 hours and >95% conversion of 4HPME to a mixture of Propanoic acid, 2-[(1S)-1-(4-hydroxyphenyl)ethoxy]-, ethyl ester, (2S)- and Propanoic acid, 2-[(1R)-1-(4-hydroxyphenyl)ethoxy]-, ethyl ester, (2S)-(EHPEP) was measured by HPLC. The reaction was slowly cooled to 5 deg. C. with mixing over 6 hours and EHPEP crystals formed.

The EHPEP crystals were isolated by filtration on a glass Buchner filter and washed with 4×200 ml aliquots of mixed hexanes. The crystals were dried overnight in vacuum oven at 25 deg. C. HPLC results indicated >99 wt. % EHPEP not including residual solvents of approximately 0.5% hexanes and 2.1 wt. % (−)-ethyl L-lactate. EHPEP yield was 188 g after drying. X-ray crystallography analyses showed the presence of both the diasteromers.

Example 2

To a 12-L round bottom glass reactor fitted with a heating mantle, thermocouple temperature indicator, overhead stirrer, vacuum, $N_2$ purge and sidearm condenser with a dry ice and isopropanol cooled glass distillate trap, 3523 g of 28 wt. % 4-hydroxyphenylmethylcarbinol (HPME) (986.44 g or 6.49 moles) in methanol and 3053 g. of (−)-ethyl L-lactate was added to achieve approximately a 15 wt. % mixture of 4HPME. The reaction contents were heated to 50 deg. C. at ~190 Torr and the methanol was removed by vacuum distillation to less than 0.1 wt. %.

To the reaction contents of 4HPME in (−)-ethyl L-lactate was added 4.25 g of a 0.402 wt. % p-toluenesulfonic acid monohydrate solution in (−)-ethyl L-lactate to achieve a pTSA concentration of 17 ppm vs. 4HPME or 2.6 ppm vs. the total contents. The pressure was held at 120 Torr and the temperature was held at 50 deg. C. The methanol byproduct was distilled from the reaction along with some (−)-ethyl L-lactate which was replaced during the reaction to maintain ~15 wt. % solids. The reaction was run for 12 hours and >95% conversion of 4HPME to a mixture of Propanoic acid, 2-[(1S)-1-(4-hydroxyphenyl)ethoxy]-, ethyl ester, (2S)- and Propanoic acid, 2-[(1R)-1-(4-hydroxyphenyl)ethoxy]-, ethyl ester, (2S)-(EHPEP) was measured by HPLC. The reaction was slowly cooled to 3.4 deg. C. with mixing over 6 hours, holding at 3.4 deg. C. for 2 hours and EHPEP crystals formed. The EHPEP crystals were isolated by filtration on a glass Buchner filter and washed with 2×800 ml aliquots of deionized water. The crystals were dried overnight in vacuum oven at 25 deg. C. HPLC results indicated 99.6 wt. % EHPEP not including residual solvents of approximately 0.2% water and 5.1 wt. % (−)-ethyl L-lactate. Total isolated EHPEP collected was 656.1 g after drying giving a yield of 42% vs. the initial 4HPME.

Example 3 and Example 4 (Comparative)

A photoresist base is prepared by dissolving 100 parts by weight of a copolymer (polyhydroxystyrene/t-butyl acrylate=70/30 by mole) and 28 parts by weight of 1,2-naphthoquinonediazido-5-sulfonic acid ester of 2,3,4,4'-tetrahydroxybenzophenone in 320 parts by weight of PGMEA. In the resulting photoresist base is dissolved EHPEP from Example 1 at a concentration of 2.50% by weight on a solid basis. The resulting solution is filtered through a 0.20 micron microfilter to prepare a photoresist composition. The photoresist composition is coated on an aluminium film-laminated silicon wafer by spin coating, and is dried at 90 C for one minute under nitrogen atmosphere in a convection oven to obtain a resist film of 1.50 microns thick. After exposure using a reduced projection exposure apparatus (248 nm projector with a standard reference pattern photomask), the resist film is developed for 1 minute with a 2.38% aqueous solution of tetramethylammonium hydroxide, is washed with water for 30 seconds and is dried. The thus formed resist pattern is observed using a standard litho evaluation using SEM to evaluate the resist quality. The above procedure is repeated again, but without the use of EHPEP. It is observed that the use of EHPEP improves the critical dimension reproduceability of this resist as compared to the repeat of this example without the use of EHPEP.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing a propanoate selected from the group consisting of (a) ethyl (2S)-2-[(1S)-1-(4-hydroxyphenyl)ethoxy]propanoate, (b) ethyl (2S)-2-[(1R)-1-(4-hydroxyphenyl)ethoxy]propanoate, and (c) mixtures of (a) and (b), which comprises the steps of (a) supplying a solution of methanol containing 4-hydroxyphenylmethylcarbinol, (b) contacting said solution with an acid ion exchange resin for a sufficient period of time and under suitable conditions of temperature and pressure to convert substantially all of said carbinol to 4-hydroxyphenylmethylcarbinol methyl ether in solution, (c) replacing the methanol in said ether containing solution with a second solvent, and (d) reacting the ether containing ethyl lactate solution with a suitable acid catalyst for a sufficient period of time and under suitable conditions of temperature and pressure to form said propanoate.

2. The process as set forth in claim 1 wherein said acid catalyst is a Lewis acid.

3. The process as set forth in claim 1 wherein the temperature in steps (b) and (d) is from about 0° C. to about 120° C.

4. The process as set forth in claim 1 wherein the acid catalyst is a mineral acid.

5. The process as set forth in claim 4 wherein the acid catalyst is sulfuric acid.

6. The process as set forth in claim 1 wherein the acid catalyst is selected from the group consisting of $H_2SO_4$, HCL, $H_3PO_4$, para-toluene sulfonic acid, methane sulfonic acid, trifluoroacetic acid, trichloroacetic acid and mixtures thereof.

7. The process as set forth in claim 1 wherein the acid catalyst is paratoluene sulfonic acid.

8. A composition of matter having the following structure:

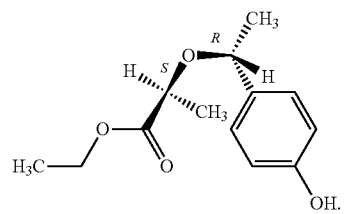

ethyl (2S)-2-[(1R)-1-(4-hydroxyphenyl)ethoxy]propanoate

9. A composition of matter having the following structure:

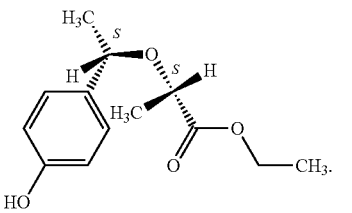

ethyl (2S)-2-[(1S)-1-(4-hydroxyphenyl)ethoxy]propanoate

10. A composition of matter comprising a mixture of the structures set forth in claims 8 and 9.

11. A composition of matter selected from the group consisting of (a) ethyl (2S)-2-[(1S)-1-(4-hydroxyphenyl)ethoxy]propanoate, (b) ethyl (2S)-2-[(1R)-1-(4-hydroxyphenyl)ethoxy]propanoate, and (c) mixtures of (a) and (b).

12. A primary photoresist composition for patterning electronic circuitry containing as an additive the composition of matter set forth in claim 11.

13. A photoresist composition comprising a styrenic polymer, an acrylate polymer and a propanoate selected from the group consisting of (a) ethyl (2S)-2-[(1S)-1-(4-hydroxyphenyl)ethoxy]propanoate, (b) ethyl (2S)-2-[(1R)-1-(4-hydroxyphenyl)ethoxy]propanoate, and (c) mixtures of (a) and (b).

14. The photoresist composition as set forth in claim 13 wherein the propanoate is present in an amount less than about 5 percent by weight based on the total weight of the polymers therein.

* * * * *